United States Patent [19]
Fujita

[11] 4,408,128
[45] Oct. 4, 1983

[54] ELECTRIC RESISTANCE TYPE WIDE RANGE MOISTURE METER

[75] Inventor: Toshio Fujita, Tokyo, Japan

[73] Assignee: Kett Electric Laboratory, Tokyo, Japan

[21] Appl. No.: 298,542

[22] Filed: Sep. 1, 1981

[30] Foreign Application Priority Data

Mar. 8, 1979 [JP] Japan .................................. 54-27206
Sep. 10, 1980 [JP] Japan ................................ 55-125849

[51] Int. Cl.$^3$ ...................... G01R 27/02; G01R 15/10
[52] U.S. Cl. .................................. 324/65 R; 324/132
[58] Field of Search ................ 324/65 R, 62, 130, 132

[56] References Cited

U.S. PATENT DOCUMENTS 3,961,247 6/1976 Toki .
3,971,984 7/1976 Bench .................................. 324/132
4,065,682 12/1977 Evans .................................. 324/132 X Primary Examiner—Stanley T. Krawczewicz
Assistant Examiner—Jose M. Solis
Attorney, Agent, or Firm—Pollock, Vande Sande & Priddy

[57] ABSTRACT

A wide range electric resistance type moisture meter is disclosed wherein a current flowing through a sample such as grain or wood is scaled by a load resistor and a feedback resistor of an operational amplifier to derive a scaled current which is proportional to the sample current, and the scaled current is current-voltage logarithmic-converted by a logarithmic conversion circuit including another operational amplifier connected to the output of the first-mentioned operational amplifier and diodes, so that a moisture content indicating voltage is linearized even in a high moisture content range. The output of the logarithmic conversion circuit is processed by an operation circuit to produce the moisture content and temperature compensated and the resulting moisture content is indicated by a moisture content indicator.

8 Claims, 11 Drawing Figures

ELECTRIC RESISTANCE TYPE WIDE RANGE MOISTURE METER

BACKGROUND OF THE INVENTION

The present invention relates to an electric resistance type moisture measurement device (hereinafter referred to as a moisture meter) for measuring the moisture content in a specimen such as wood, grain, particularly wheat (hereinafter referred to as a sample) by utilizing a correlation with the electric resistivity of the sample, and more particularly to a wide range moisture meter which allows a linear indication of moisture content even when the moisture content of the sample is as high as 40% and the electric resistivity thereof reduced exponentially.

Figure 1:
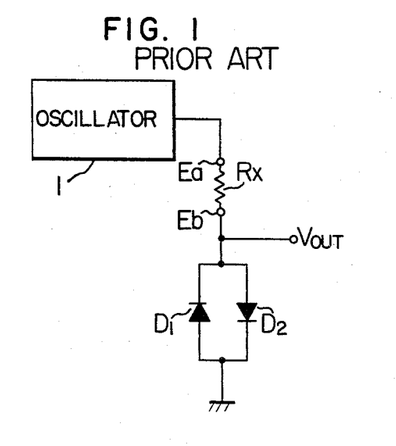
FIGS. 1 and 2 show circuit diagrams for explaining principles of prior art electric resistance type moisture meter.

In a prior art electric resistance type grain moisture meter, it has been proposed to increase a reading accuracy by using an equi-spaced indicator scale because the relation between the moisture content of the grain and the electric resistivity is non-linear as the moisture content varies between a low moisture content and a high moisture content. For example, a moisture measurement circuit as shown in FIG. 1 has been proposed, in which a power supply 1 such as an oscillator is provided, diodes $D_1$ and $D_2$ are connected in series with a sample $R_X$ to apply a constant voltage from the power supply 1 so that an output $V_{out}$ which is a combination of a logarithmic characteristic of a forward voltage of the diode and a logarithmic characteristic of the moisture contained in the grain versus the electric resistance is produced to attain a linear indication of the moisture content. However, in such a system, when the moisture content is as high as 30% or more, an impedance of the sample reduces to as low as several hundreds ohms. Thus, if an applied voltage is, for example, 8 volts, an excessive current in the order of several tens milliamperes flows through the sample, and when the current is logarithmic converted the output is saturated and the joule heat generated by the current flowing through the diodes $D_1$ and $D_2$ affects the measured output. In addition, a voltage drop of approximately 400–800 millivolts is developed across the logarithmic conversion element such as diodes and transistor. When a constant voltage is applied, the voltage drop changes with the current and hence a voltage across the sample connected in series with the logarithmic conversion element also changes. Thus, when the applied voltage is low, an error is included in the logarithmic conversion. A basic circuit of such measurement circuit is disclosed in the U.S. Pat. No. 3,961,247 assigned to the assignee of the present application.

Figure 2:
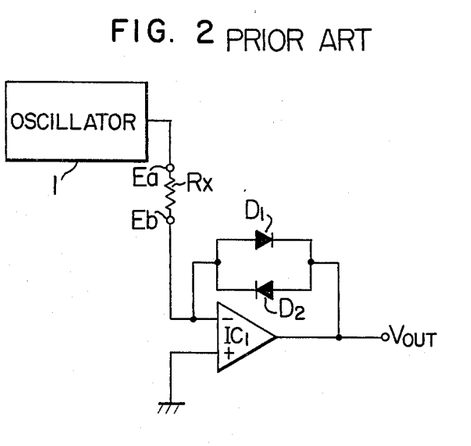

FIG. 2 shows a linear current-voltage conversion circuit, in which an A.C. power supply, an operational amplifier $IC_1$ and logarithmic conversion diodes $D_1$ and $D_2$ as a feedback circuit are provided, and a current flowing into the operational amplifier $IC_1$ depends on a sample resistance and most of the current flows into the feedback current so that an output voltage is determined by a product of a resistance of the diodes $D_1$ and $D_2$ serving as logarithmic conversion elements and a current flowing therethrough. As a result, a substantially constant voltage is applied to the sample but the output varies in a high moisture content region because of the influence of joule heat in the diodes $D_1$ and $D_2$. In addition, in the circuit of FIG. 2, since a current of several tens milliamperes flows in the high moisture content region, the logarithmic converted output may saturate and the linearity may be lost.

SUMMARY OF THE INVENTION

It is, therefore, an object of the present invention to provide an electric resistance type moisture meter which overcomes the problems discussed above and allows the indication of a wide range moisture content by an equi-spaced scale as required by shunting a sample current within a range which permits a linearity of a logarithmic conversion in a correlation function of the sample current and a moisture when the moisture content is high and the sample current is hgih.

It is another object of the present invention to provide a wide range electric resistance type moisture meter which allows the measurement of the moisture in a low moisture content region and a high moisture content region ranging from 10% to 40% without a manual switching operation.

In order to achieve the above objects, in accordance with one aspect of the present invention, a current flowing through a sample upon application of a constant voltage is divided to a load resistor and a feedback resistor by an operational amplifier and a current proportional to the sample current is current-voltage logarithmic converted to that a linear voltage indication of the moisture is attained with a high accuracy even in a high moisture content region.

In accordance with another aspect of the present invention, the current flowing through the sample upon application of a content voltage is not scaled in a low moisture content region, but it is directly logarithmic-converted, and in the high moisture content region the current is directed to a scaling circuit through an analog switch and the scaled current is logarithmic-converted, and the analog switch is automatically selected by the scaled moisture signal so that a wide range of sample moisture content is measured without a manual switching operation.

DESCRIPTION OF THE PREFERRED EMBODIMENTS

The preferred embodiments of the present invention will now be described with reference to the accompanying drawings.

Figure 3:
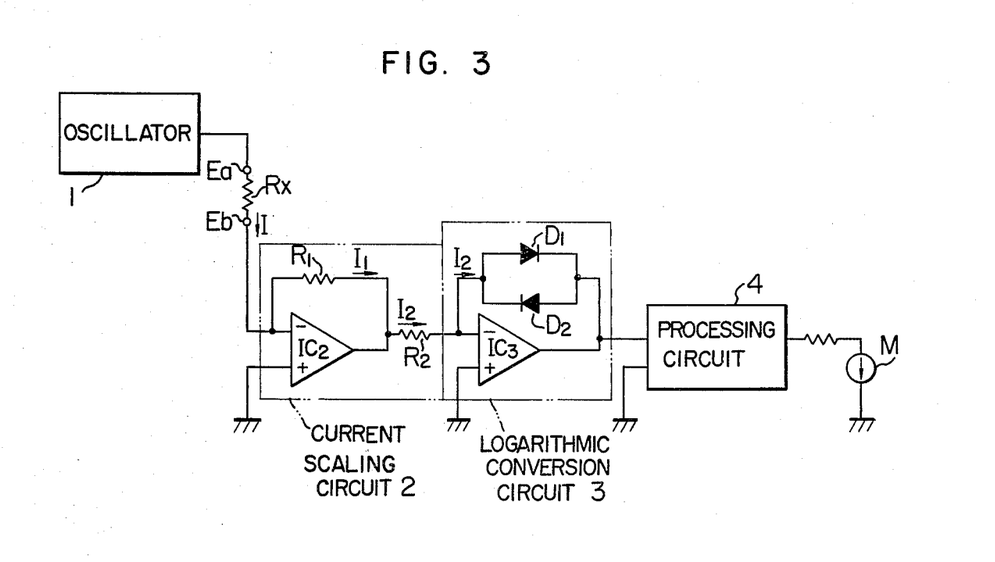
FIG. 3 shows a circuit diagram of a wide range moisture meter in accordance with one embodiment of the present invention.
Figure 3A:
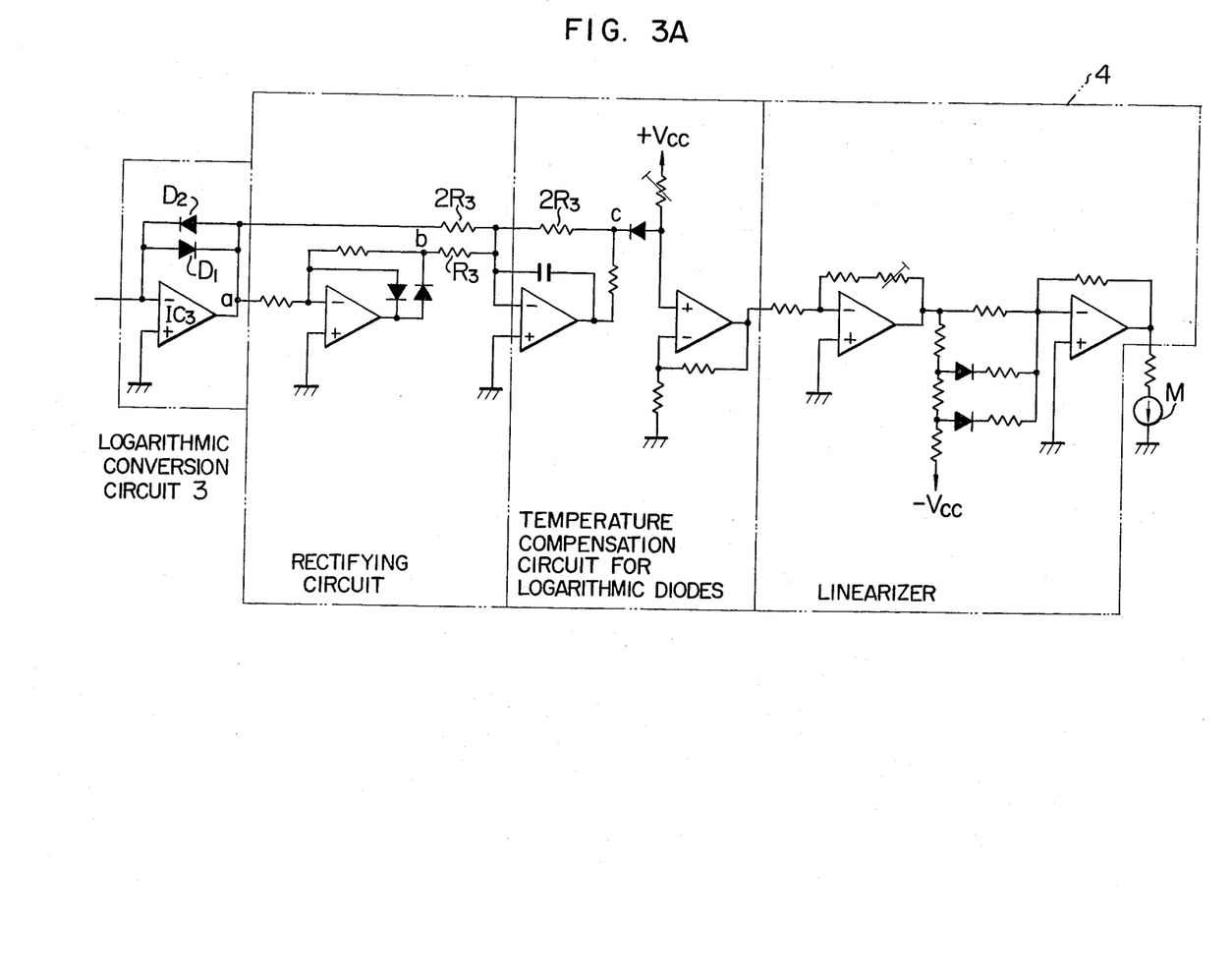
FIG. 3A shows an example of the processing circuit illustrated in FIG. 3.

FIG. 3 shows a measurement circuit of an electric resistance type moisture meter in accordance with the present invention. In FIG. 3, an oscillator 1 is a D.C. or A.C. constant voltage source which may be, for example, a power supply of a frequency of 80 Hz and a voltage Eo of 8 volts. A pair of electrodes Ea and Eb which accommodate ground sample grain such as wheat are connected to the constant voltage source oscillator 1 and an inverting input of an operational amplifier IC$_2$ of a current scaling circuit 2. A non-inverting input of the operational amplifier IC$_2$ is grounded. A resistor R$_1$ of 200Ω and a load resistor R$_2$ of 5.1 KΩ are connected to an output of the operational amplifier IC$_2$, and the other terminal of the resistor R$_1$ is connected to the inverting input of the operational amplifier IC$_2$ to form a negative feedback circuit of the amplifier IC$_2$ while the other terminal of the resistor R$_2$ is connected to an input of a succeeding stage logarithmic conversion circuit 3. As a whole, they form the current scaling circuit 2 which scales an input current I to currents I$_1$ and I$_2$ which flow through the resistors R$_1$ and R$_2$, respectively. The operational amplifiers IC$_2$ and IC$_3$ may be of FET type, e.g. Intersil ICL 7621 DCPA. An output of the current dividing circuit 2 is supplied to the succeeding stage logarithmic conversion circuit 3 though the load resistor R$_2$ which serves as a coupling resistor. The smaller the current scaling ratio is, the larger is the S/N ratio, but it has to be determined while taking a current limitation to the logarithmic conversion elements into consideration. The logarithmic conversion circuit 3 may be basically the configuration as shown in FIG. 1 or any other known circuit. For example, in the block 3 of FIG. 3, the coupling resistor R$_2$ is connected to the one input of the current-voltage converting operational amplifier IC$_3$ and logarithmic converting diodes D$_1$ and D$_2$ are connected in a feedback path of the amplifier IC$_3$. At an output of the amplifeir IC$_3$, the sample current is logarithmic-converted to a voltage which substantially linearly represents the moisture content. The output is further amplified by a processing circuit 4 which may include a linearizer for linearizing the output, and an output of the amplifier 4 is indicated by an equi-scaled D.C. ammeter M or digitally indicated by a counter indicator. FIG. 3A shows a detail of an embodiment of the processing circuit 4.

A principle of the operation of the circuit of FIG. 3 is explained below. A current I$_1$ flowing through the sample is represented by I$_1$=E$_o$/R$_X$, where R$_X$ is an electrical resistance which correlates to the moisture contained in the sample. The current scaling ratio which is determined by the resistors R$_1$ and R$_2$ of the current scaling circuit 2 is 1/25 in the present example, and the scaled current I$_2$ is supplied to the logarithmic conversion circuit 3. A substantial portion of the current I$_2$ flows into the feedback diodes D$_1$ and D$_2$. In selecting the resistances of the resistors R$_1$ and R$_2$, the lower limit of the measured output voltage from the opamp IC$_2$ should be selected such that an offset voltage of the opamp IC$_3$ and the effect of a temperature drift are not large. The scaled current I$_2$ is represented by:

$$|I_2| = \frac{R_1}{R_2}|I_1| = \frac{R_1}{R_2} \cdot \frac{|E_o|}{R_X}$$

Accordingly, the output voltage V of the logarithmic conversion circuit is expressed by:

$$V = \frac{-KT}{q}(\ln|I_2| - \ln I \text{ const})$$

$$= \frac{-KT}{q}\left(\ln\frac{R_1|E_o|}{R_2} - \ln I \text{ const} - \ln R_X\right)$$

$$= \frac{-KT}{q}(\ln C - \ln R_X)$$

where q is a charge, k is the Boltzmann constant, T is an absolute temperature, I const is a reverse saturation current and C is a constant. Since $$\ln C = \ln\frac{R_1 E_o}{R_2} - \ln I \text{ const is constant,}$$

it can be rendered to zero by an appropriate zero adjustment by the processing circuit 4. Thus, by neglecting it, the output voltage V of the circuit 3 is proportional to the logarithmic function of the sample resistance R$_X$. The processing circuit 4 further functions to compensate for a temperature dependency which would otherwise cause a measurement error and linearize the output.

Figure 4:
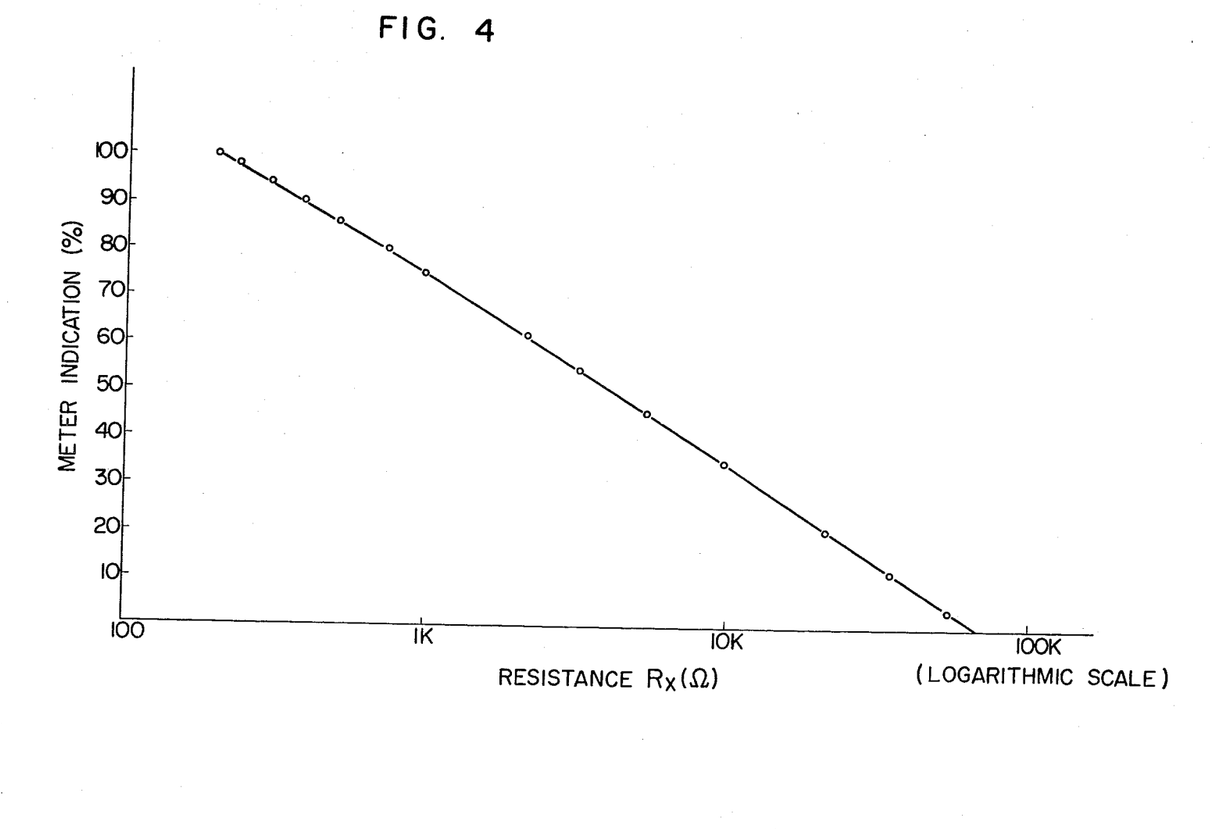
FIGS. 4 and 5 show characteristic charts measured for the moisture meter of FIG. 3.
Figure 5:
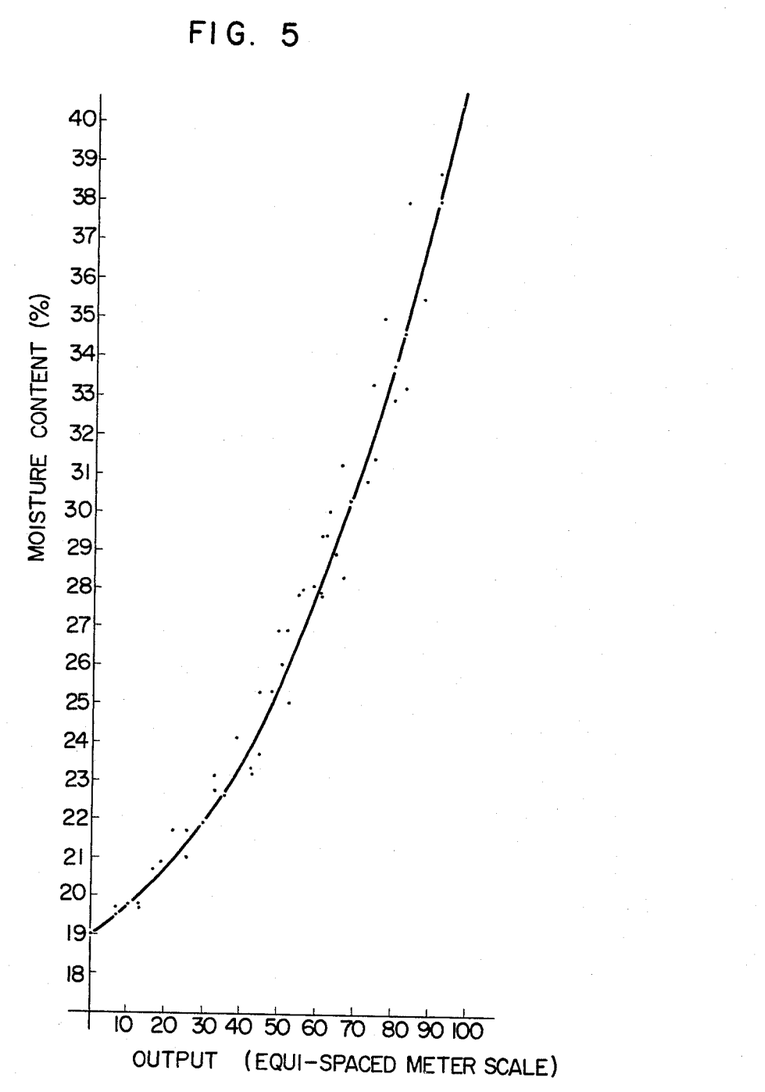

FIG. 4 shows a linear relation between the equivalent resistance R$_X$ and the meter indication when various standard resistors equivalent to sample resistance are inserted between the electrodes Ea and Eb of the moisture meter device in accordance with the present embodiment. FIG. 5 shows a result of the measurement of the moisture content measured for the wheat using the above device. An ordinate represents the moisture content in percent and an obscissa represents the indication of the meter in 100 equi-spaced scale. It should be understood to those skilled in the art that a non-linear portion of the illustrated characteristic can be converted to a linear relation by an appropriate process in the processing circuit 4.

As described above, in the prior art logarithmic conversion circuit having the combination of the operational amplifier and the diodes as shown in FIG. 2, the applied voltage must be maintained low, and for the sample such as grain which has very complex internal structure and which is affected by polarization phenomenon, a satisfactory accuracy is not attained. The measurement for the moisture content region of 30% or higher is not possible. In fact, in the prior art moisture meter, the upper limit for the moisture measurement is 30% and the sample resistance therefor is 2-3 KΩ. If the moisture content increases to 40%, the sample resistance decreases to as low as 400Ω. Thus, since the variation range of the resistor is very wide, a desired measurement is not attained by simply using the constant current source or lowering the applied voltage. On the other hand, in the present embodiment, by providing the operational amplifier IC$_2$ preceding to the essentially conventional current-voltage logarithmic conversion circuit and scaling the sample current by the feedback resistor R$_1$ and the load resistor R$_2$, a wide range of grain moisture content up to 40% or more can be measured with a high accuracy. Furthermore, as shown in FIG. 3A, by providing the linearizer between the current-voltage logarithmic conversion circuit and the indicator, the linearity can be assured between the moisture content converted to the electric signal and the indication scale. The linearizer shown in FIG. 3A is of segment approximation type comprising the operational amplifier and two diodes. Where parallel-connected resistors are connected in series with the electrodes Ea and Eb instead of using the operational amplifier $IC_2$ in the current scaling circuit 2, it is necessary to select a small parallel resistance because of the need for maintaining the voltage across the sample electrodes at a constant level. In such a case, it has been found that the influence by the succeeding stage operational amplifier $IC_3$ is too large to attain a desired scaled current measurement. The device of the present embodiment is also applicable to the measurement of high-moisture containing sample other than grain, such as wood.

In the measurement circuit of the present embodiment, it is difficult to measure the moisture in a low moisture content region because of the influence by the offset voltages of the operational amplifiers (in the order of several millivolts) and the temperature drifts (in the order of 10 $\mu V$-20 $\mu V/°C.$). This is because the current flowing through the sample $R_X$ is in the order of 100 nA in the low moisture content region and hence the output voltage of the amplifier $IC_2$ reduces to approximately 20 $\mu V$ when $R_1$ is 200Ω and the feedback resistor $R_1$ should have a resistance of 200Ω because of the necessity of the current scaling in the high moisture content region. The following embodiment resolves the above problem.

Figure 6:
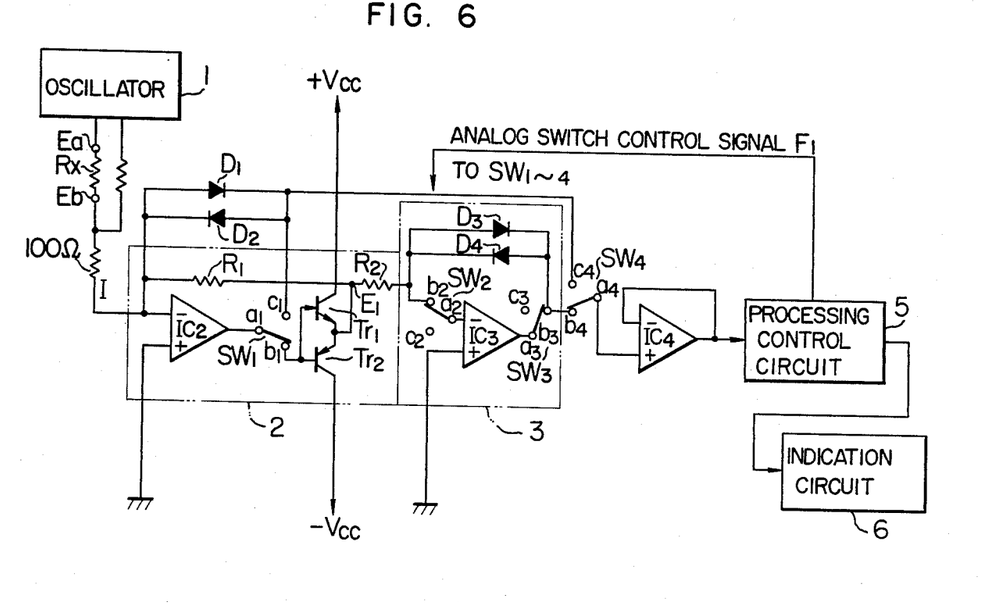
FIG. 6 shows a circuit diagram of another embodiment of the present invention.

FIG. 6 shows a measurement circuit of the electric resistor type moisture meter in accordance with another embodiment of the present invention. An oscillator 1 is a D.C. or A.C. constant voltage source which may be a power supply having a frequency of 80 Hz and a voltage Eo of 8 volts. A pair of electrodes Ea adn Eb which accommodate ground sample grain such as wheat are connected to the oscillator 1 and an inverting input of operational amplifier $IC_2$ of a current scaling circuit 2. A non-inverting inptu of the operational amplifier $IC_2$ is grounded. An output of the amplifier $IC_2$ is connected to an analog switch $SW_1$ which may be Hitachi HD14053B C-MOS. The analog switches $SW_1$-$SW_4$ each has an electronically movable contact $a_i$ and fixed contacts $b_i$ and $c_i$ (where $i=1$-4). In an initial state, the contacts $a_1b_1$, $a_2b_2$, . . . are connected to form a high moisture content measurement circuit. The contact $b_1$ is connected to a current booster circuit comprising transistors $Tr_1$ and $Tr_2$. The booster circuit assures the output current of the operational amplifier in the order of several tens milliamperes. A resistor $R_1$ forms a feedback circuit of the operational amplifier $IC_2$, and an output voltage $E_1$ at the junction of the feedback resistor $R_1$ and a load resistor $R_2$ is a product of the current I and the resistance $R_1$, that is, $E_1=R_1I$.

A block 3 represents a current-voltage logarithmic conversion circuit which comprises an operational amplifier $IC_3$ and logarithmic diodes $D_3$ and $D_4$. A current of $$\frac{R_1}{R_2} \times I$$

flows through the resistor $R_2$ into the logarithmic conversion circuit 3 by the analog switches $SW_2$ and $SW_3$ connected between the operational amplifier $IC_3$ and the contacts $a_2$ and $b_2$ and the contacts $a_3$ and $b_3$, respectively. That is, the current I flowing through the sample scaled by the ratio of $R_1/R_2$ flows. The scaled current is then supplied to a processing-control circuit 5 through the analog switch $SW_4$ and a voltage buffer circuit $IC_4$.

When the measured moisture signal is determined as of the low moisture content region by the circuit 5, an analog switch selecting signal is produced to switch the analog switches $SW_i$ ($i=1$-4) so that the paths between the contacts $a_i$ and $c_i$ are closed. Thus, the current flowing through the sample is directly applied to a logarithmic amplifier comprising the operational amplifier $IC_2$ and the diodes $D_1$ and $D_2$ and it is logarithmic-converted. The resulting voltage is supplied again to the processing-control circuit 5 through the voltage buffer circuit $IC_4$ and then supplied to an indication circuit 6 which indicates the resultant moisture content, through a linearizer, not shown. In this manner, the current scaling circuit 2 is eliminated in the measurement of the low moisture.

In FIG. 6, the switches $SW_2$ and $SW_3$ may be omitted and instead the switching circuits may be directly connected and a switch having a low turn-on resistance such as a relay may be inserted between the resistor $R_1$ and the input of the operational amplifier $IC_2$. In this modification, a noise supplied to the inverting input of the operational amplifier $IC_2$ from $R_1$, $R_2$, $D_3$ and $D_4$ in the measurement of the low moisture content can be reduced.

Figure 7:
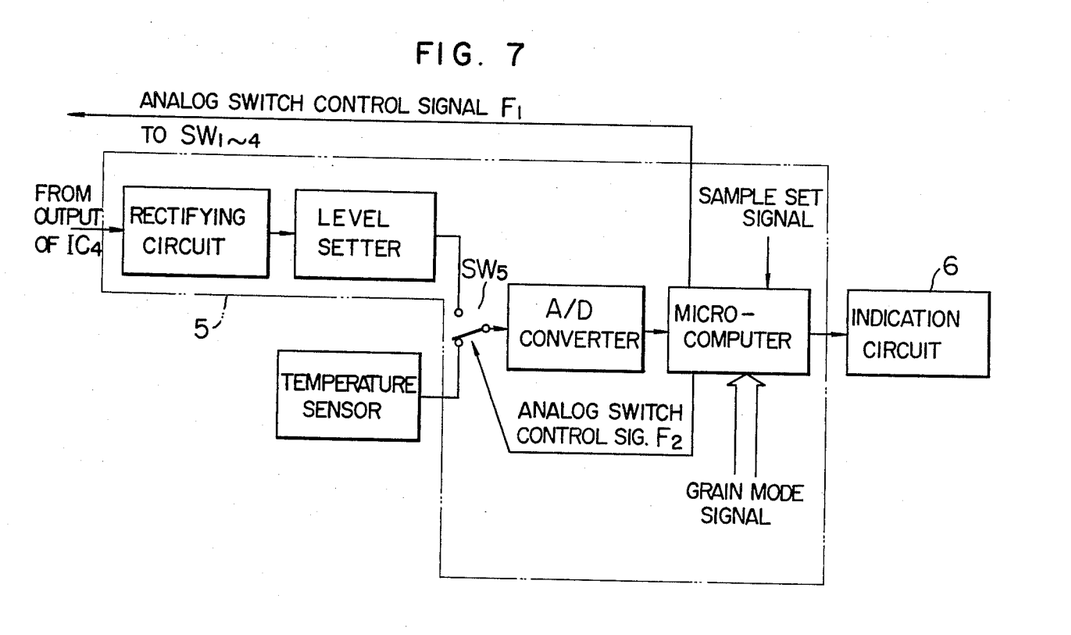
FIG. 7 shows a circuit diagram of a processing-control circuit shown in FIG. 6.

FIG. 7 shows an example of the processing-control circuit 5. The processing-control circuit 5 comprises a rectifying circuit which receives an analog measured moisture data from the amplifier $IC_4$, a level setter, an analog switch $SW_5$ for selecting the moisture data and a temperature signal, and A/D converter and a microcomputer. The microcomputer may be a 4-bit C-MOS microcomputer such as Hitachi HMCS 43C. When the sample is not inserted between the electrodes Ea and Eb, a sample set signal assumes a LOW level and a control signal $F_2$ renders the analog switch $SW_5$ to a reset state so that a temperature signal from a temperature sensor used to temperature-compensate the sample moisture content is supplied to the microcomputer. When the sample is inserted between the electrodes Ea and Eb, the sample set signal assumes a HIGH level and the analog switch $SW_5$ is switched to a moisture data input position. The A/D converted moisture data is applied to the microcomputer which carries out a moisture operation for converting the moisture data to a moisture content in accordance with a grain mode input, and a temperature compensation operation. Based on the input signal level, the microcomputer determines whether the sample moisture is in the low moisture content region or the high moisture content region and produces an analog switch control signal $F_1$ to switch the analog switches $SW_1$-$SW_4$.

Figure 8:
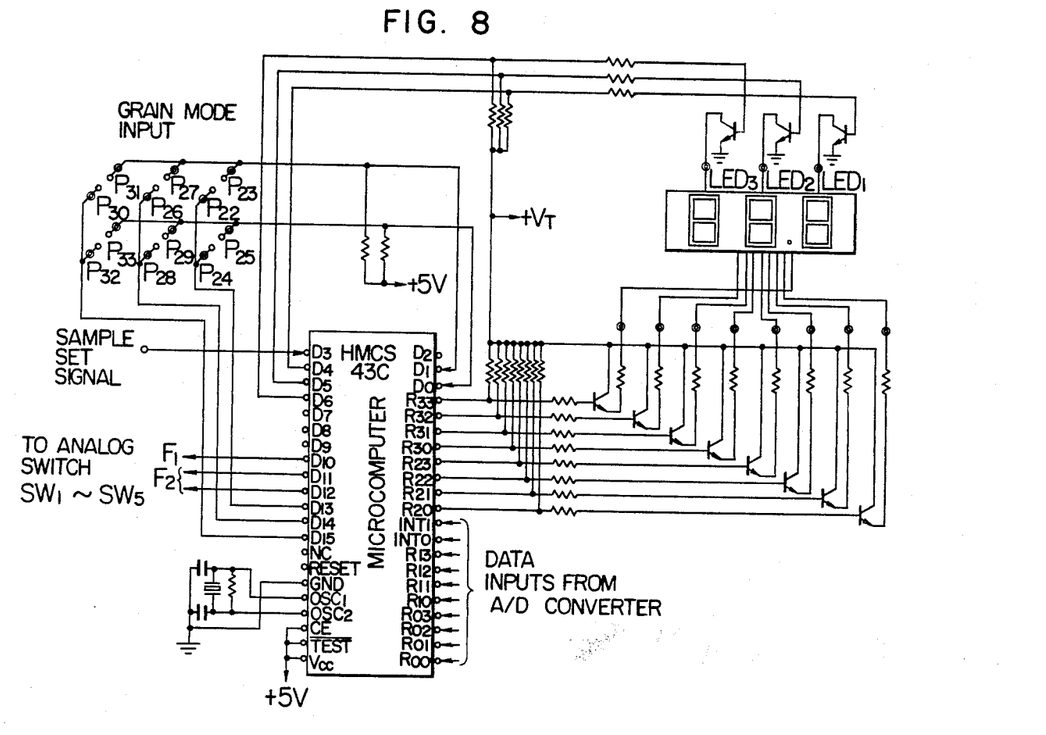
FIG. 8 shows connection of external terminals of a microcomputer.
Figure 9:
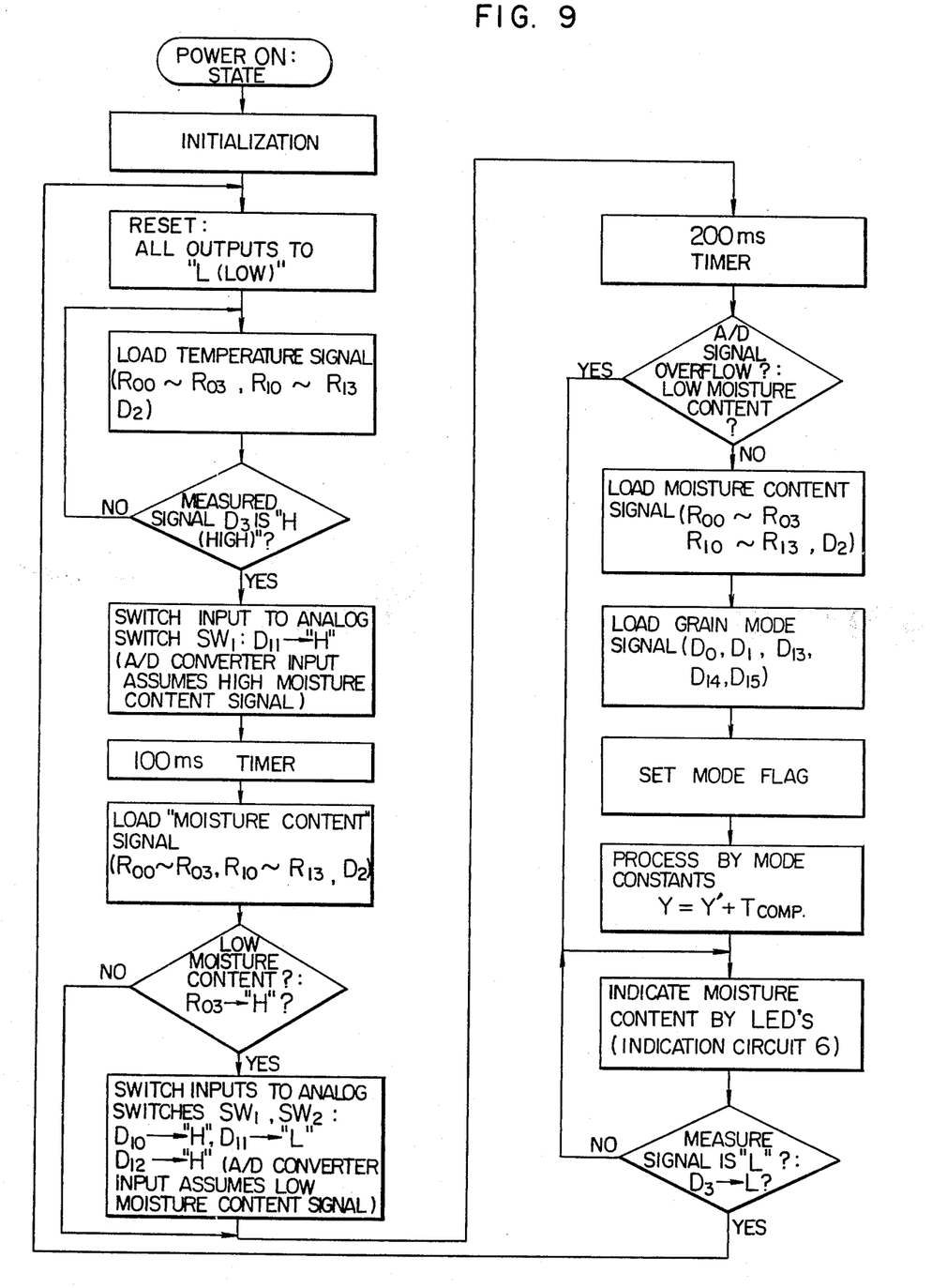
FIG. 9 shows a flow chart illustrating the operation of the circuits of FIGS. 7 and 8.

FIG. 8 shows connections of external terminals of the microcomputer shown in FIG. 7, to which an LED digital indicator circuit is coupled for the moisture content indication circuits 6, and a flow chart of FIG. 9 illustrates the operation of the circuit. In the flow chart of FIG. 9, a moisture content Y is determined by $Y=Y'+T$ comp in the moisture content operation in accordance with constants determined by a particular grain mode, where $Y'=A_o+A_1X+A_2X^2+A_3X^3$, X is the input signal indicative of moisture data from the A/D converter and $A_o$-$A_3$ are constants depending on the type of grain, which are constants of a return line determined by the moisture content and X which in turn are determined by sample tests. The grain mode is set by pins $P_{22}$-$P_{33}$. T comp is a sample temperature compensation factor.

Instead of using the microcomputer for determining whether the measured input signal is in the low moisture content region or the high moisture content region, a signal taken from the output of the output operational amplifier of the temperature compensation circuit of FIG. 3A may be supplied to a comparator comprising an operational amplifier, a resistor and a capacitor to produce a control signal indicating the low moisture content range.

Figure 10:
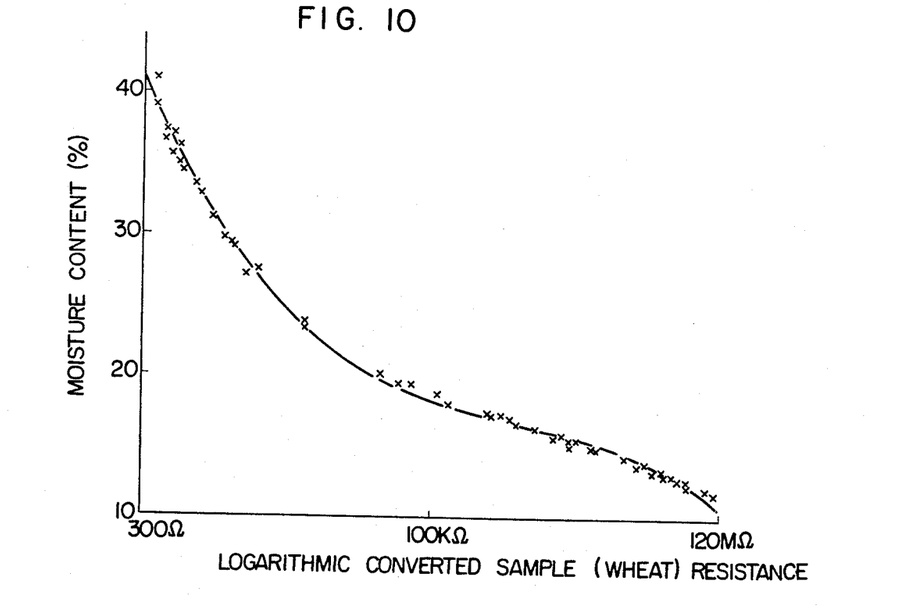
FIG. 10 shows a resistance-moisture characteristic chart for wheat sample.

FIG. 10 shows a resistance-moisture characteristic chart for a sample wheat when it is gradually dried, in which an ordinate represents a moisture content in percent and an abscissa represents a logarithmic-converted sample resistance.

In accordance with the present invention, the sample moisture in a wide dynamic range from several hundreds ohms to several hundreds meg-homs, which could not be measured by the prior art moisture meter, can be automatically measured. The present invention is particularly suitable in digitally indicating the measured data.

What is claimed is:

1. In an electric resistance type moisture measurement apparatus comprising a means for measuring the electric resistance of a sample to be measured, a current-voltage logarithmic conversion means coupled to said resistance measuring means for converting a current flowing through the sample when a constant voltage is applied thereto to a voltage signal as a moisture content corresponding to the measured electric resistance and converting an expoential characteristic of the moisture content signal to an essentially linear characteristic, and an indicator means for indicating the converted signal outputted from said conversion means in terms of the moisture content, a wide range moisture content measuring device comprising an operational amplifier having a current feedback path, connected between said resistance measuring means and said current-voltage logarithmic conversion means, said operational amplifier including a load resistor and a feedback resistor, whereby a current flowing through said sample is scaled into said resistors and the scaled current flowing through said load resistor is supplied to said current-voltage logarithmic conversion means.

2. A wide range moisture content measuring device according to claim 1 wherein said constant voltage is supplied by a D.C. or A.C. power supply.

3. In an electric resistance type moisture content measuring apparatus in which a moisture content ratio of a sample charged in measuring electrodes corresponding to an electric reistance thereof is represented by a voltage derived from a current-voltage logarithmic conversion means which converts a current flowing through the sample when a constant voltage is applied thereto to the voltage, converts an exponential characteristic of the moisture content to an essentially linear characteristic, and the converted moisture content is indicated by an indicator, a wide range moisture content measuring device comprising;

switching means for selectively connecting a current scaling circuit between said measuring electrodes and said current-voltage logarithmic conversion means in a high moisture content region, and control means for generating a switching signal for said switching means to cause said switching means to directly connect said measuring electrodes to said current-voltage logarithmic conversion means when the output of said current-voltage logarithmic conversion means is a low moisture content signal.

4. A wide range moisture content measuring device according to claim 3 wherein said switching means are analog switches.

5. A wide range moisture content measuring device according to claim 3 or 4 wherein said constant voltage applied to said measuring electrodes is supplied by a D.C. or A.C. power supply.

6. A wide range moisture content measuring device according to claim 3 wherein said control means includes an A/D converter for converting the output of said current-voltage logarithmic conversion means and a microcomputer responsive to the output of said A/D converter for determining if said output is the low moisture content signal or not to produce an indication signal.

7. A wide range moisture content measuring device according to claim 3 wherein said control means includes a comparator for comparing the output of said current-voltage logarithmic conversion means and a reference indicating a boundary of the low moisture content region, said comparator producing a compare signal for switching said switching means when said output is the low moisture content signal.

8. A wide range moisture content measuring device according to claim 6 wherein said microcomputer calculates the moisture content depending on a type of the sample to digitally indicate the moisture content on said indicator.

* * * * *